LITTLELEAF LINDEN

Filed April 7, 1965 3 Sheets-Sheet 1

INVENTOR.
DAVID B. COLE
BY
Oberlin, Maky & Donnelly
ATTORNEYS

LITTLELEAF LINDEN
Filed April 7, 1965 3 Sheets-Sheet 2
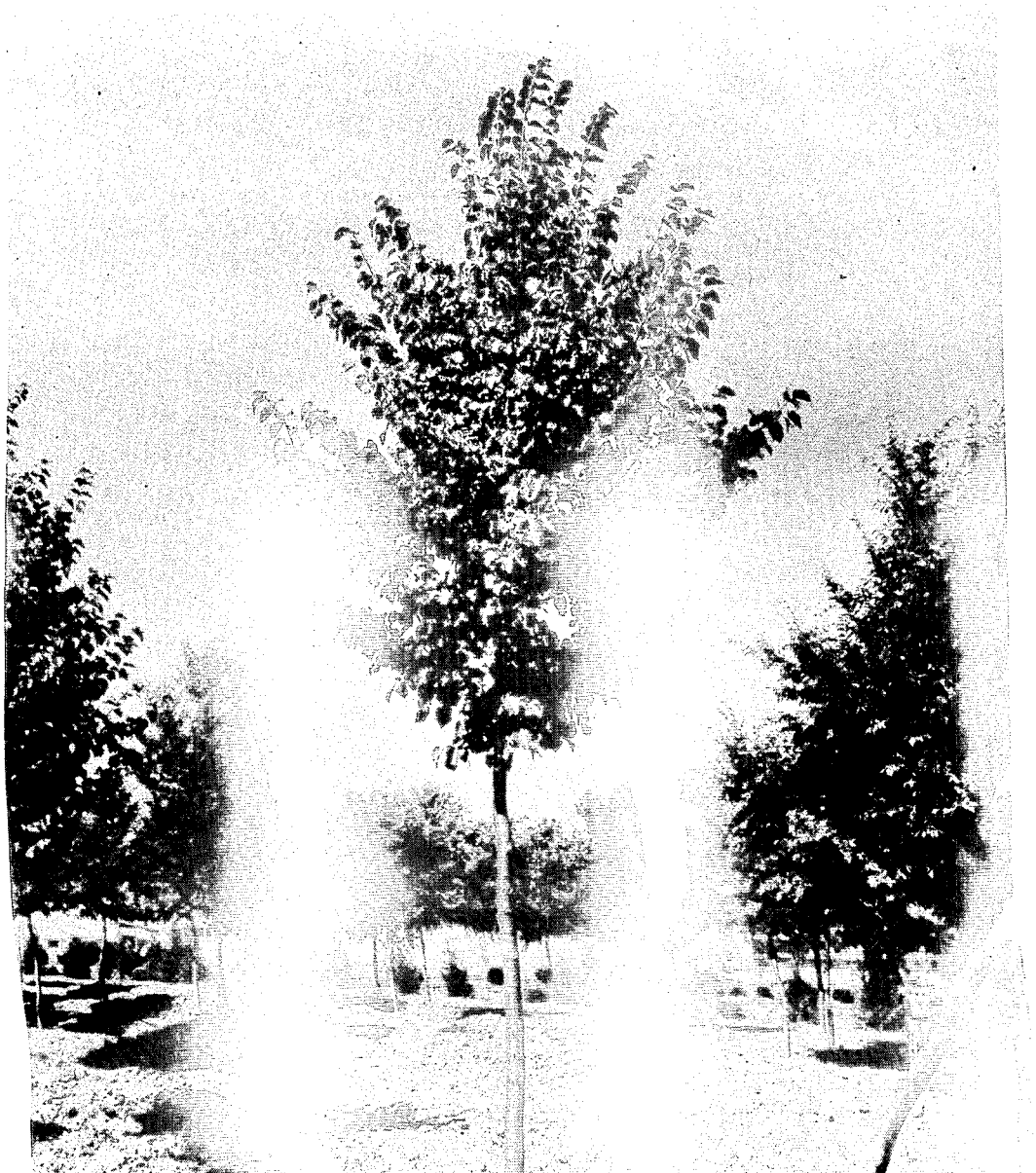

United States Patent Office

Plant Pa

Patented Feb.

1

2,712

LITTLELEAF LINDEN

David B. Cole, Mentor, Ohio, assignor to The Cole Nursery Company, Mentor, Ohio, a corporation of Ohio

Filed Apr. 7, 1965, Ser. No. 446,442
1 Claim. (Cl. Plt.—51)

The present invention relates to a new and distinct variety of Littleleaf Linden tree (*Tilia cordata*) which was originated by me as a selected seedling from a large planting of seedlings made by me.

The new variety of Littleleaf Linden tree which I have thus produced has the following combination of characteristics which serve to distinguish it from other seedling trees of the species and other varieties known to me.

The tree of my invention is of compact, upright and relatively narrow pyramidal habit of growth, and this outstanding characteristic is consistently transmitted to its asexually propagated progeny.

The trees of this clone are rapid growing as compared to seedling Littleleaf Lindens grown in the same area under the same cultural conditions, making height especially quickly when young and they give an indication of maturing at a height of approximately 35 feet when used as a city street tree in the area of Cleveland, Ohio. Trees which were budded at Painesville, Ohio, from the original clone in 1957 had a caliper at 12 inches above the ground of about 4 inches seven years later, with a height of from 18–20 feet and an average crown width of approximately 6 feet.

General habit of the tree is upright and compact, the branches being most attractively and quite evenly spaced around the trunk, in contrast with seedling trees which usually have the branches arranged in flat planes. Numerous small twigs are formed along the branches and branchlets.

While the tree will broaden somewhat with age, nevertheless present indications are that it will develop into a mature tree having a width or spread of only about 60 percent of that of the usual *Tilia cordata*.

In the annexed drawing:

FIG. 2 shows the same tree during the growing season of its seventh year; and

FIG. 3 shows typical leaves of this tree.

Figure 1:
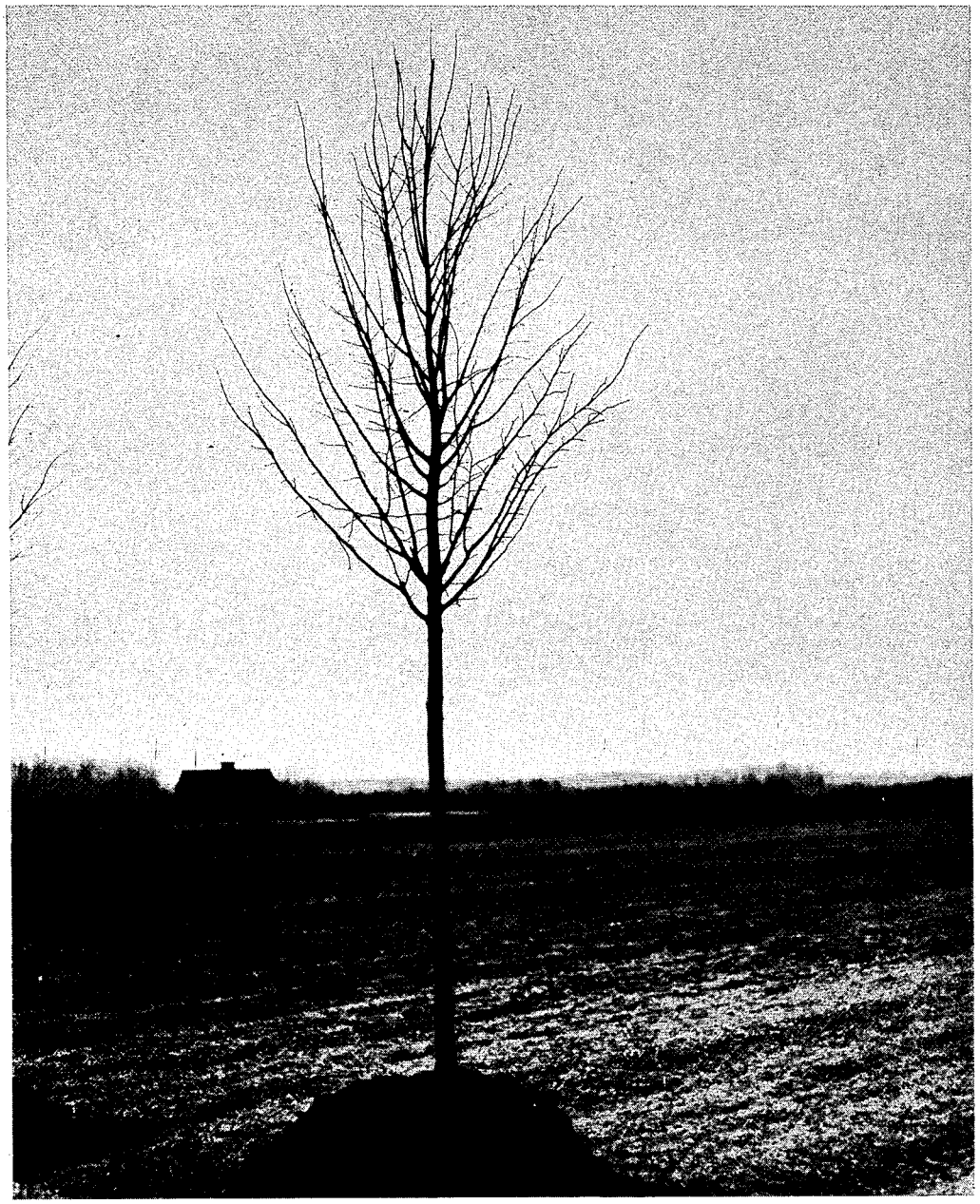
FIG. 1 shows a typical specimen of my new variety seven years of age in dormant condition.

As shown in the drawing, the trunk of the tree is very erect and straight, and the branches consistently emerge therefrom at an upward angle of from about 45° to about 30° from the vertical, with relatively few sharper angles. The tree has shown itself to be very resistant to storm damage. As is apparent from the drawing, the tree is of desirable and attractive form with good distribution and density of branches, in contrast to some known varieties having an excessive number of branches too closely spaced for satisfactory development over the years.

The bark color of immature one-year twigs as noted in late September is light to medium olive-brown with a greenish undercolor, sometimes tinted reddish-brown on

2 the upper or sunny side. The color of dorma twigs is brown to light reddish-brown, and th two- to four-year-old branches is medium to tinged with gray or green.

The upper surfaces of the leaves are dark g ly glossy and smooth. The undersides of the a somewhat lighter green with a whitish or g being smooth but not shiny. Tufts of brown on such undersides where the 5–7 main ribs petiole, and are also occasionally present whe ribs join the main midrib. Typical leaves ar FIG. 3 of the drawing, and it may be noted tha leaf lobes are frequently of unequal length, The leaf blade length averages about 2½ to 3 i a width of 2 to 2½ inches, and the petiole 1¼ inches. The foliage has an exceptionall pearance and is therefore more attractive than and the leaves are more densely set than in t trees. In fact, as late as mid-September 1964, were still a remarkably attractive deep gree spite of a rather dry season accompanied by sev of extremely hot drying winds. This resistance weather and drought conditions constitutes o superior characteristics of this new tree when to other unnamed seedlings and cultivars of *Ti* of the same age grown at the same site under culture conditions.

The flowers are typical for the species, bein and normally appearing in late June or early Ju ern Ohio).

The fruit likewise appears typical for the spec an average length of bract (with the petiole) 2¼ to 2½ inches. The average number of bract is five, and the average length of the s inch. The color of the mature fruit is a light

I claim:

A new and distinct variety of Littleleaf L (*Tilia cordata*) substantially as herein shown scribed, characterized particularly as to nove straightness of trunk, high density of foliage an pact, relatively narrow pyramidal upright branches emerging radially from the trunk at tial upward angle and then turning still more in direction at an angle of from about 45° to from the vertical forming a symmetrical tree side. Resistance to adverse weather and dr exceptional.

References Cited by the Examiner

UNITED STATES PATENTS

P.P. 2,086 9/1961 Flemer ----------

OTHER REFERENCES

Scanlon: "Tailored" Trees, Wholesale List N 1963/Spring 1964, page 82 relied on.

ABRAHAM G. STONE, *Primary Examiner.*

R. E. BAGWILL, *Assistant Examiner.*

Feb. 14, 1967 C. L. VINYARD Plant Pat. 2,713
PLUM TREE
Filed Oct. 19, 1965
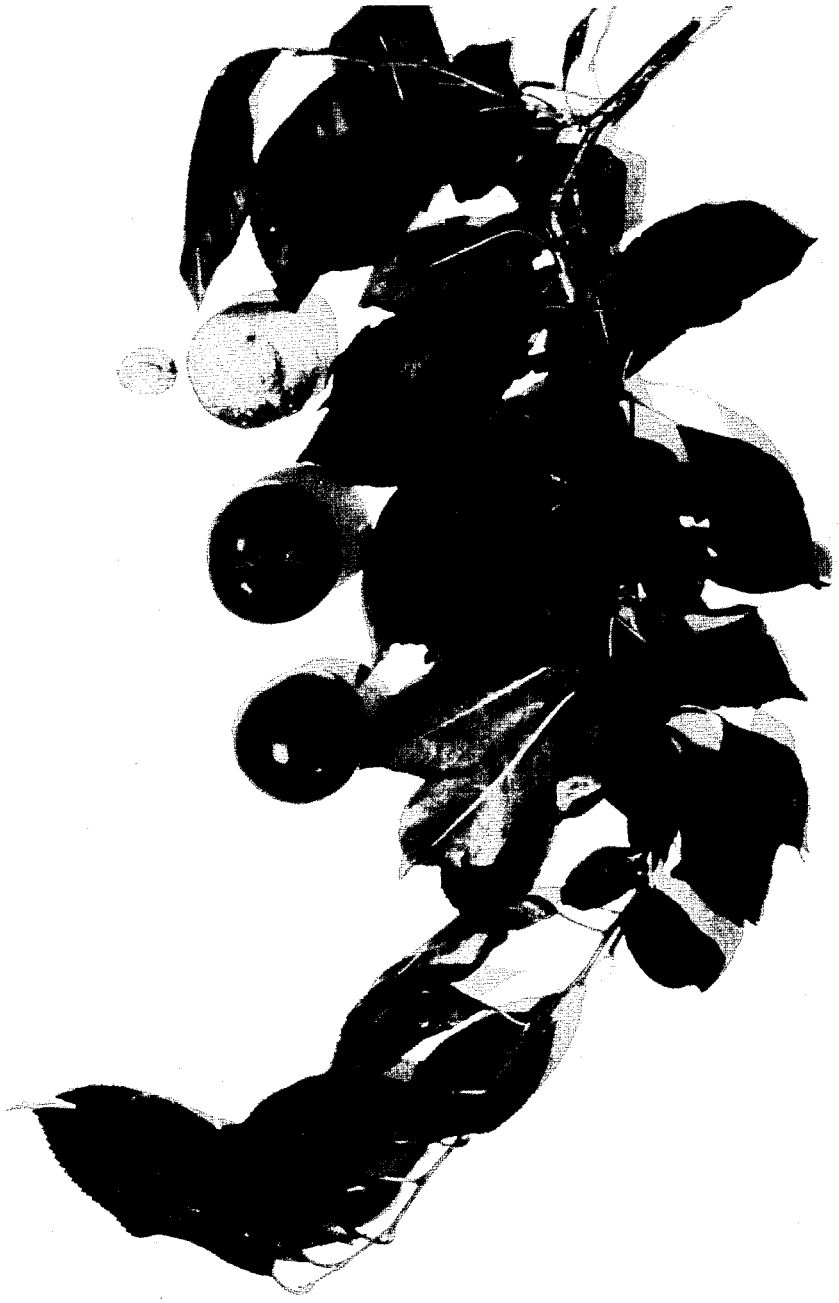
CHARLES L. VINYARD
INVENTOR
Huebner & Worrel
ATTORNEYS